United States Patent

Paul et al.

[19]

[11] Patent Number: 5,944,744
[45] Date of Patent: Aug. 31, 1999

[54] IMPLANTABLE CARDIAC STIMULATOR WITH AUTOMATIC ELECTROGRAM PROFILING

[75] Inventors: Patrick J. Paul; David Prutchi, both of Lake Jackson, Tex.

[73] Assignee: Sulzer Intermedics Inc., Angleton, Tex.

[21] Appl. No.: 09/019,751

[22] Filed: Feb. 6, 1998

[51] Int. Cl.$^6$ .................................................. A61N 1/37
[52] U.S. Cl. .............................. 607/9; 600/523; 600/509; 607/2
[58] Field of Search .................................. 607/2, 4, 5, 9, 607/13, 27, 28, 32; 600/509, 519, 521, 523

[56] References Cited

U.S. PATENT DOCUMENTS

| | | | |
|---|---|---|---|
| 4,779,617 | 10/1988 | Whigham | 607/9 |
| 4,830,006 | 5/1989 | Haluska et al. | 128/419 |
| 4,903,699 | 2/1990 | Baker, Jr. et al. | 128/419 |
| 4,913,145 | 4/1990 | Stotts | 128/419 |
| 5,024,221 | 6/1991 | Morgan | 128/419 |
| 5,103,819 | 4/1992 | Baker et al. | 128/419 |
| 5,314,453 | 5/1994 | Jeutter | 607/61 |
| 5,564,430 | 10/1996 | Jacobson et al. | 600/510 |
| 5,722,999 | 3/1998 | Snell | 607/27 |

OTHER PUBLICATIONS

W. Brunekreeft, Initial Experience with the Saphir Single Lead VDD/R System, pp. 1–10, 1994, The Netherlands.
Intermedics Inc., Tomorrow's Technology Today, Mar. 1996, 4 pages, Angleton, Texas.
Intermedics Inc., Autosensing Manages Dynamic Sensing Thresholds, Jan. 1996, 2 pages, Angleton, Texas.
Intermedics Inc., Autosensing, Mar. 1996, 4 pages, Angelton, Texas.

Primary Examiner—William E. Kamm
Assistant Examiner—Kennedy J. Schaetzle
Attorney, Agent, or Firm—Schwegman, Lundberg, Woessner & Kluth, P.A.

[57] ABSTRACT

An implantable medical device for electrically stimulating the heart to beat generally includes a processor, a plurality of electrodes, a sense amplifier, a pair of comparators, inner and outer target logic units, and pulse generator. The processor controls the magnitudes of inner and outer target reference signals which are generated by the inner and outer target logic units, respectively. The outer target is adjusted to be approximately equal to the peak amplitude of the cardiac signal. The processor stores representations of the outer target reference in memory. Alternatively or additionally, the processor computes a histogram of the relative or absolute number of cardiac cycles that occur over a given period of time for each outer target setting. The processor can be directed to retrieve the outer target representations and/or the histogram from memory and transmit that information to an external programmer for use by a physician.

9 Claims, 6 Drawing Sheets

IMPLANTABLE CARDIAC STIMULATOR WITH AUTOMATIC ELECTROGRAM PROFILING

BACKGROUND OF THE INVENTION

A. Field of the Invention

The present invention relates generally to cardiac stimulating devices. More particularly, the present invention relates to an implantable cardiac pacemaker or cardioverter/defibrillator.

B. Description of the Related Art

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. Furthermore, to determine what pacing rate is required by the pacemaker, rate-responsive demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three or four letters. A fifth coded position may be used to describe a pacemaker's ability to respond to abnormally high heart rates (referred to as tachycardia). Because most pacemakers do not provide any antitachycardia functions, the fifth coded position is not used in most commonly used pacemaker types. Thus, most common configuration codes comprise either three or four letters, as shown in Table I below. For this reason and for simplicity's sake, the fifth code position is omitted from the following table. Each code can be interpreted as follows:

TABLE I

| Code position | 1 | 2 | 3 | 4 |
| --- | --- | --- | --- | --- |
| Function Identified | chamber paced | chamber sensed | response to sensing | programmability, rate modulation |
| Options Available | 0 - none<br>A - atrium<br>V - ventricle<br>D - dual<br>(A + V) | 0 - none<br>A - atrium<br>V - ventricle<br>D - dual<br>(A + V) | 0 - none<br>T - triggered<br>I - inhibited<br>D - dual<br>(T + I) | 0 - none<br>P - programmable<br>M - multi-programmable<br>C - communicating<br>R - rate modulating |

For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activation of the ventricle (i.e., the ventricle paces itself naturally). In VVIR mode, ventricular pacing is similarly inhibited upon determining that the ventricle is naturally contracting. With the VVIR mode, the pacer's pacing rate, however, in the absence of naturally occurring pacing at an appropriate rate, is modulated by the physical activity level of the patient. Pacers commonly include accelerometers to provide an indication of the patient's level of physical activity.

As illustrated in the table above, it may be desired to sense in one cardiac chamber (i.e., detect electrical activity representative of contraction of the chamber and referred to as a "sensed event") and, in response, pace (referred to as a "paced event") in the same or a different chamber. In general, most pacemakers today incorporate a sensing function to detect electrical activity at the site of one or more electrodes. The sensing circuit in the pacemaker (often referred to as the "sense" circuit) receives the electrical signals from the electrodes and determines when a physiologically significant event has occurred. Accordingly, if the heart's natural pacemaker is able to make the heart beat properly, the pacemaker's sense circuit detects the naturally occurring electrical impulses and determines that the heart is beating properly on its own.

Most pacemaker sense circuits incorporate an amplifier that amplifies the electrical signals received from the electrodes. Sense circuits typically also incorporate, or are coupled to, a comparator circuit that compares the magnitude of the amplified signal received from an electrode to a reference signal. When the amplified signal from the electrode exceeds the amplitude of the reference signal, the pacemaker determines that a physiologically significant event has occurred. In this context, the physiologically significant events are cardiac events, such as a contracting heart chamber. It is important for a pacemaker to accurately determine when a cardiac event has occurred. That is, a pacemaker should detect a true cardiac event, but not respond to non-cardiac signals.

In early pacemakers, the thresholds of the sense circuit were set during manufacture. However, preset thresholds often resulted in inappropriate pacing therapy because the amplitude of the electrical events in the heart varies widely from one patient to another. Further, changes in the amplitude of the electrical signals are common in the same patient as a result of a variety of factors, such as encapsulation of the electrode by fibrotic tissue, movement of the lead, changes and deterioration of the lead and other lead-related issues. In addition, the amplitude of the cardiac signal will vary due to changes in the electrophysiology of the heart. This latter effect is most drastic at the onset and progression of tachycardia (abnormally fast heart rate) and fibrillation (complete lack of blood pumping capacity), which are accompanied by a relatively rapid and sustained change in the amplitude of cardiac electrical events. For bradycardia (excessively slow rate) applications, large variations in a portion of the cardiac signal commonly referred to as the "P-wave" may occur as a result of patient movement and respiration, particularly when the patient's atrial electrodes are not anchored unto the heart wall, but "float" in a chamber.

In order to cope with these amplitude variations in the cardiac signal, some implantable cardiac stimulators include threshold circuits that are programmable by an attending physician. Such devices normally store information regarding the amplitude of the cardiac electrical signals in memory incorporated within the implant. While a patient is at a medical facility, a physician is able to establish a communication link to the implanted device with the aid of external programmer. The amplitude information stored previously by the implanted device is then transmitted to the external programmer. The physician analyzes this data and reprograms the implanted device's sense circuit to a suitable sensing threshold.

Other implanted devices include "automatic gain control" ("AGC") in which the implanted device is itself able to determine and select a suitable threshold setting without requiring the assistance of an external programmer and attending physician. Various AGC methods have been suggested and generally are useful for coping with the fast changing cardiac signal amplitudes characteristic of certain diseases and conditions. Although AGC methods attempt to track the cardiac signals and adapt the sense thresholds automatically in an optimal manner, limiting their operating range is nevertheless required to ensure that noise, artifacts or other electrical signals are not detected as electrical events originating from the heart chamber to which the sense circuit is associated. The limits imposed on present day AGC methods are determined based on the observed amplitudes of the cardiac signals. Thus, whether or not a cardiac stimulator employs AGC, it is desirable to provide to a physician information regarding the observed cardiac signal amplitudes.

Until now, implantable cardiac stimulators have included dedicated circuitry to measure and track the cardiac signal amplitude. Such circuitry is usually quite complex, consumes battery power, and depletes the limited space inside the implanted device. Because implantable cardiac stimulators normally are powered by a limited-life battery, it is desirable for the implant to consume as little power as possible. Further, the device should be as small and reliable as possible. With these design goals in mind, it is always desirable for an implantable medical device to include as few components as possible to minimize the number of components that can fail, thereby increasing reliability. Further, an implant with fewer components will generally consume less electrical power.

Accordingly, there is a need for an implantable cardiac stimulator that provides cardiac signal amplitude information to an external programmer using simpler and more reliable circuitry. Such a device would preferably include fewer circuit components compared to prior art devices. Despite the advantages such a device would offer, to date no such device is known to exist.

SUMMARY OF THE INVENTION

Accordingly, there is herein provided an implantable medical device, such as a pacemaker or implantable cardioverter/defibrillator, that electrically stimulates the heart to beat and monitors the electrical activity of the heart. The medical device includes a sense amplifier, a filter, at least two comparators, inner and outer programmable target logic units, a pulse generator, and a processor. The processor is programmable to automatically adjust the sensitivity of the sense amplifier to a level suitable for the patients' cardiac signal. Accordingly, the processor directs the programmable target logic units to generate desired target reference signals. The inner target logic unit generates an inner target reference and the outer target logic unit generates an outer target reference.

Based on control signals from the processor, the programmable target logic units adjust the target reference signals to provide optimal sensitivity for detecting and processing the patients' cardiac signal. Accordingly, the processor directs the outer target logic unit to adjust the outer target reference signals to a level that closely approximates the peak amplitudes of the amplified cardiac signal. Thus, the outer target reference signal can be used as an indication of the peak amplitude of the cardiac signal.

The processor preferably stores representations of the outer target reference in memory, and alternatively, or additionally, computes a histogram of the relative absolute number of cardiac cycles per period of time for each outer target setting and stores the histogram in memory. This information, the representations of the outer target or the histogram, can be retrieved by the processor and transmitted to an external programmer for use by a physician.

BRIEF DESCRIPTION OF THE DRAWINGS

Other objects and advantages of the invention will become apparent upon reading the following detailed description and upon reference to the accompanying drawings, wherein.

DETAILED DESCRIPTION OF THE PREFERRED EMBODIMENTS

Figure 1:
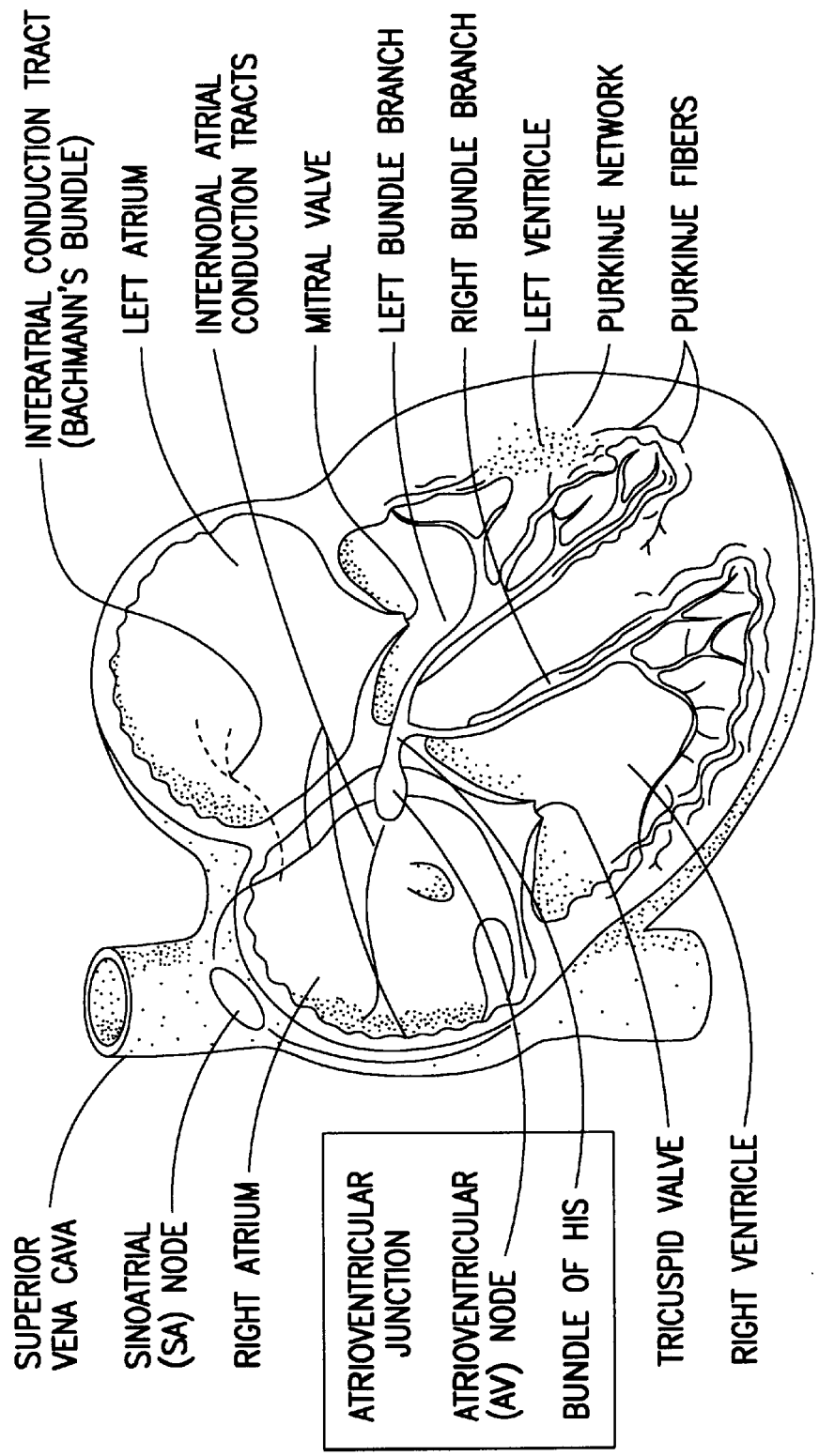
FIG. 1 is a schematic cut-away view of a human heart, in which the various relevant parts are labeled.
Figure 2:
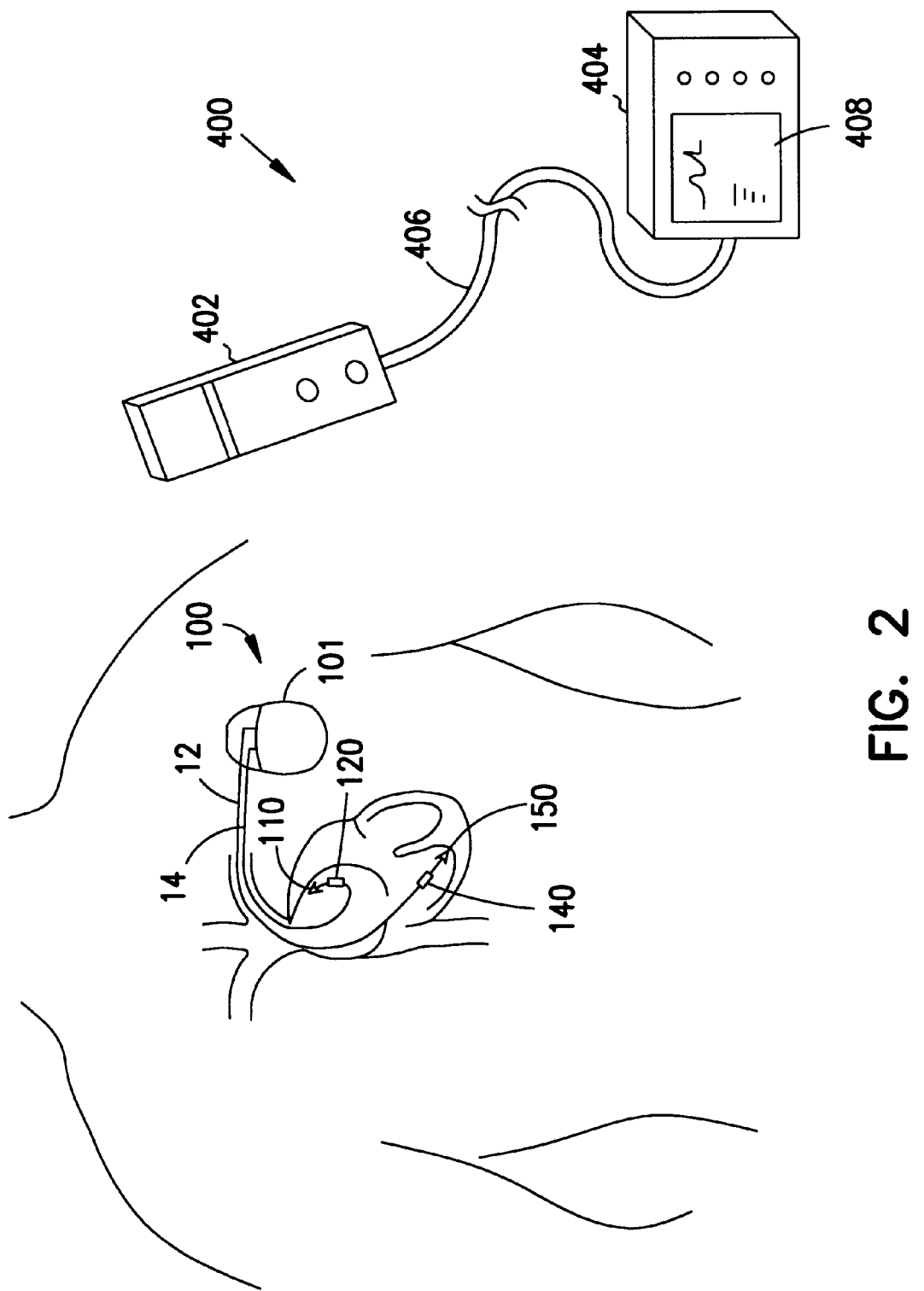
FIG. 2 is a schematic diagram of an implantable medical device constructed in accordance with the present invention and implanted in a human body and of an external programmer used to communicate with the implantable device.

Referring now to FIG. 2, an implantable medical device 100 constructed in accordance with the preferred embodiment is shown implanted and coupled, in an exemplary configuration, to the patient's heart by leads 12, 14. Medical device 100 also communicates with an external programmer 400. The implantable medical device 100 may include a pacemaker or any medical device that performs pacing functions, including many defibrillators. For purposes of describing the preferred embodiments of the invention, however, the implantable medical device 100 will hereafter be described as an implantable pacemaker or simply pacer. However, it should be understood that the invention may be employed in any of a variety of implantable medical devices, such as defibrillators.

The arrangement shown in FIG. 2 represents a dual chamber pacing configuration in which two leads 12 and 14 are coupled to a housing or "can" 101. In the configuration shown, the leads 12, 14 are positioned in two chambers of the heart, lead 12 implanted in the right ventricle and the other lead 14 implanted in the right atrium. Each lead may incorporate any desired number of electrodes. The leads 12, 14 shown in FIG. 2, for example, are bipolar leads meaning each lead includes two electrodes. Lead 14 includes a tip cathode electrode 110 and a ring anode electrode 120. Lead 12 includes a tip cathode electrode 150 and a ring anode electrode 140. As one skilled in the art will understand, two, three, and four lead devices all have been used or suggested as various pacemaker configuration schemes and may be employed in the present invention. Further, the pacemaker can 101 itself can be used as an electrode. The configuration shown in FIG. 2 is intended to be exemplary only of the many electrode and lead configurations possible for use with pacemaker 100.

A communication link exists between the pacer 100 and the external programmer 400. The programmer 400 generally includes a hand-held "wand" 402 connected to a control unit 404 via an umbilical cable 406. The control unit 404 includes a display 408 through which a physician or medical technician can view status and data related to the pacer 100. After placing the wand 402 on or near the patient's skin over the site of the implanted pacer 100, the programmer 400 can be activated by a physician or technician to establish communication with the pacer. Subsequently, control and data signals may be transmitted bidirectionally between the pacer 100 and programmer 400.

Any one of a number of communication techniques may be implemented for the communication link between the pacer 100 and programmer 400. In accordance with a preferred embodiment, however, the communication link is established between a pair of coils of wire (shown in FIG. 3 as coils 111, 403). Coil 111 is attached to or contained within the implanted pacer 100 and the other coil 403 is contained within the external wand 402. An alternating current generated in one coil creates electromagnetic waves that, in turn, induce a current in the other coil. Information is transmitted via the electromagnetic waves by modulating the current in the transmitting coil in accordance with a predetermined modulation technique. An exemplary communication technique is described in detail in U.S. Pat. No. 5,314,453, incorporated herein by reference.

Figure 3:
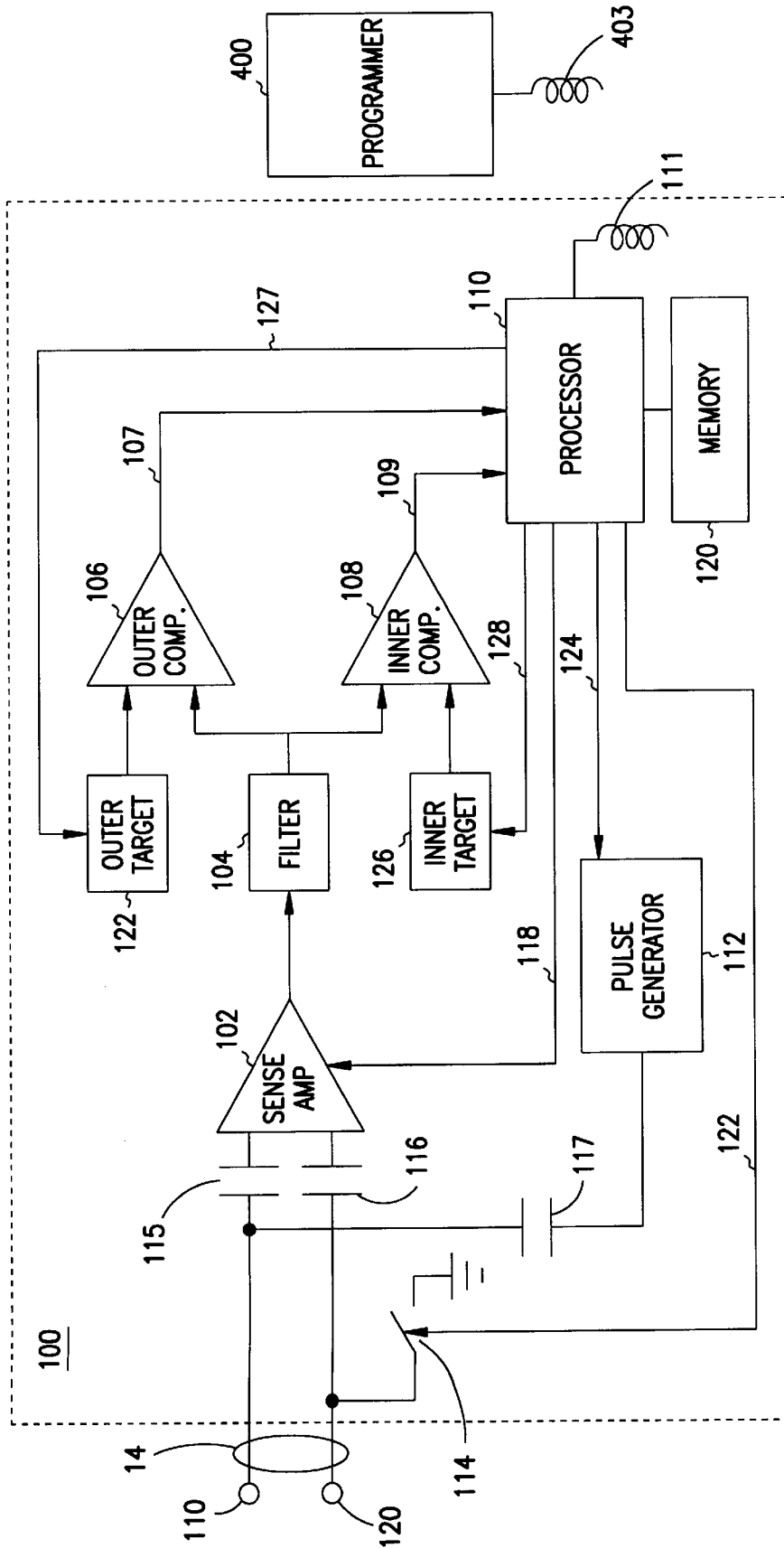
FIG. 3 is a block diagram of the implantable medical device of FIG. 2 including programmable target logic units.

Referring now to FIG. 3, the components of the pacer 100 particularly relevant to the invention generally include a sense amplifier 102, a filter 104, an outer comparator 106, an inner comparator 108, a processor 110, a pulse generator 112, a memory 120, and programmable target logic units 122, 126. It should be recognized that pacer 100 may include other components that are not specifically shown in FIG. 3. Further, the embodiment of the invention shown in FIG. 3 is illustrated with respect to electrodes 110 and 120 of lead 14, but may include additional electrodes such as electrodes 140, 150 of lead 12 (FIG. 2). Additional sense amplifiers, filters, and comparators also may be incorporated as desired.

The sense circuit of the pacer 100 generally includes the sense amplifier 102, filter 104 and outer and inner comparators 106, 108. These components generally function to condition signals received from electrodes 110, 120 on lead 14. Sense amplifier 102 amplifies the signal from the electrodes 110, 120, and preferably is a low power amplifier operating from a power supply of approximately one microampere of current. A suitable sense amplifier is disclosed in U.S. Pat. No. 4,913,145, and incorporated herein by reference.

Filter 104 preferably is a band pass filter implemented as a switched capacitor configuration. Band pass filter 104 generally passes signals from its input terminal to its output terminal whose frequencies are within a predetermined range (or "band") of frequencies, and attenuates signals whose frequencies are outside the filter's frequency band. Filter 104 processes the amplified signal from sense amplifier 102 by attenuating those frequencies that are known not to include relevant cardiac signals. Filter 104, however, generally cannot attenuate non-cardiac signals whose frequencies are within the filter's frequency band. Also, filter 104 preferably includes a full-wave rectifier known to those of ordinary skill so that comparators 106, 108 will be triggered by positive and negative excursions of the intracardiac electrogram (IEGM). An example of a suitable filter 104 is described in U.S. Pat. No. 5,024,221, incorporated herein by reference, although any other low power, reliable filter suitable for use in implantable pacemakers may also be employed.

Comparators 106, 108 preferably are also low power devices, such as that described in U.S. Pat. No. 4,913,145. Each comparator compares the voltage provided to it on its non-inverting (+) terminal with the voltage on its inverting (−) terminal. Each comparator generates a logic high output signal on its output line 107 or 109 if the non-inverting (+) input voltage is greater than the inverting (−) voltage or, conversely, a logic low output signal if the inverting (−) voltage is greater than the non-inverting (+) voltage.

The processor 110 preferably controls the operation of pacer 100 and may include any suitable low power micro-controller or micro-processor. The processor 110 receives signals from the comparators 106, 108 over signal lines 107, 109, controls the sensitivity setting of the sense amplifier 102 via control line 118, controls the configuration of switch 114 via control line 122, and via control line 124 determines when a pacing pulse should be delivered to the heart from the pulse generator 112 through the electrodes 110, 120.

A reference voltage is provided to the inverting (−) terminals of comparators 106, 108 by programmable target logic units 122, 126. Programmable outer target 122 provides an outer target reference signal to outer comparator 106, and programmable inner target 126 provides an inner target reference signal to inner comparator 108. The processor 110 also controls the magnitude of the reference voltages via control lines 127 and 128. The magnitude of each reference signal is programmed via control signals from processor 110 on lines 124, 128. Accordingly, the processor 110 can independently set the outer and inner target references by providing appropriate control signals on lines 127, 128 to programmable target logic units 122 and 126, respectively.

The pulse generator 112 generally includes suitable circuitry to generate an electrical pulse that has sufficient energy to cause a desired cardiac chamber to contract. Accordingly, pulse generator 112 generates a voltage pulse whose amplitude and time duration may be up to 8 volts and 1.5 milliseconds, or other suitable combinations of voltage and time. The pulse generator 112 may also include a pacing rate limiter for safety to ensure the processor 110 does not erroneously attempt to pace the heart at an excessively high rate.

Referring still to FIG. 3, electrodes 110, 120 couple to the sense amplifier 102 and the pulse generator 112 via capacitors 115, 116, 117. Capacitors 115, 116, 117 can be any suitable value but capacitors 115, 116 preferably are 0.15 microfarad capacitors and capacitor 117 preferably is a 10 microfarad capacitor.

The communication link between the implanted pacer 100 and external programmer 400 is illustrated schematically by coils 111 and 403 as discussed above. Communication preferably is bidirectional. That is, data and/or control signals may be transmitted from the programmer 400 to the pacer 100 and from the pacer to the programmer.

Processor 110 preferably includes both volatile and non-volatile memory. Non-volatile memory, in which the memory's contents are not erased when power is turned off, is used to store executable instructions for the processor 110 as well as various fixed parameters and control values. Volatile memory, whose contents disappear when power is removed, is used as a temporary storage for variables and data to be transmitted via coil 111 to programmer 400. In addition, pacer 100 may also include memory 120 separate from processor 110 to provide further temporary storage capacity. In fact, memory 120 may be necessary if processor 110 does not include any volatile memory.

In accordance with the preferred embodiment, pacer 100 includes any suitable automatic gain or sensitivity control capability. The automatic sensitivity control assures proper sensing of cardiac activity. To accomplish this task, pacer 100 uses two sensitivity levels. One sensitivity level corresponds to the inner target reference voltage provided by programmable inner target 126, and the other sensitivity level corresponds to the outer target reference voltage provided by programmable outer target 122.

Figure 4:
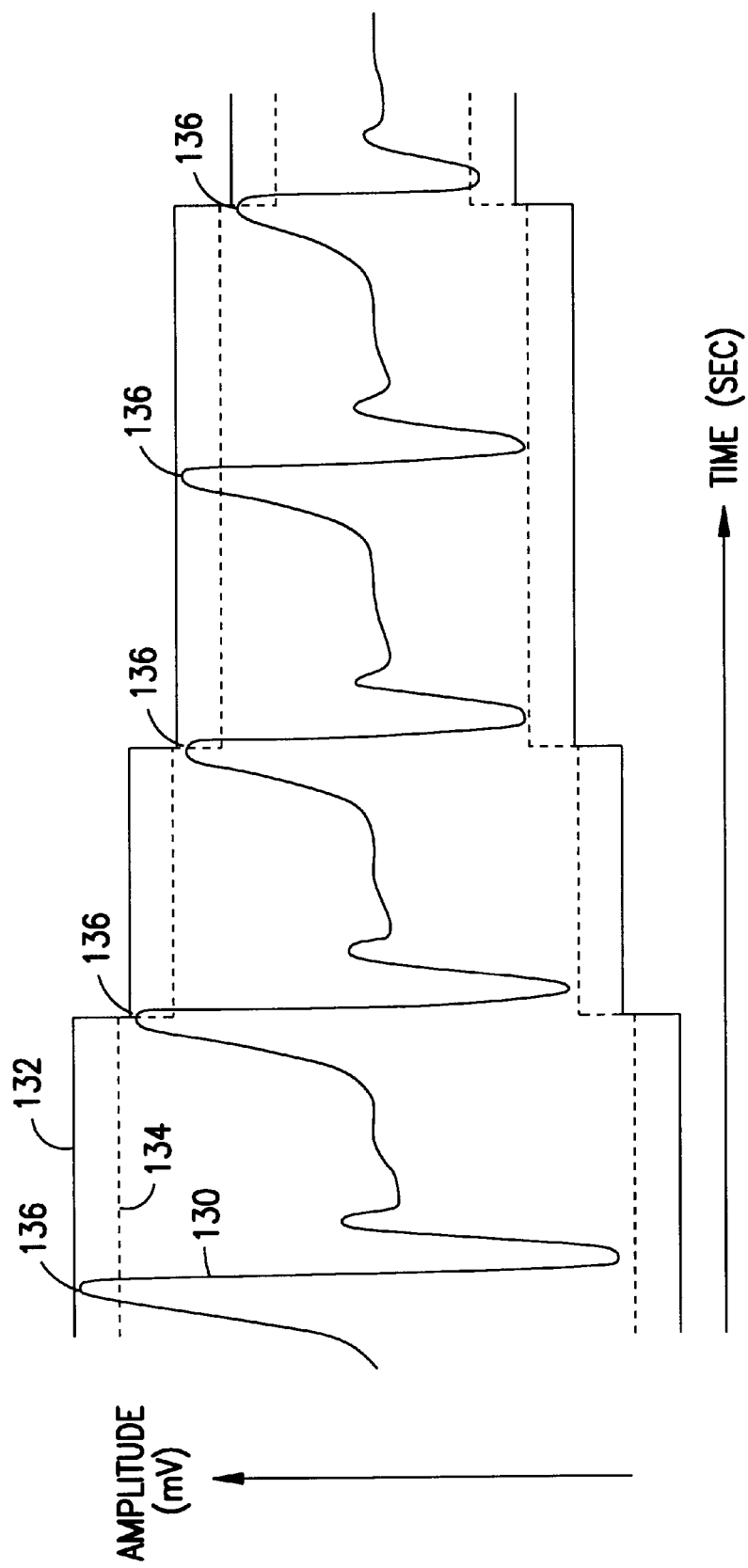
FIG. 4 is an exemplary cardiac electrical signal in relation to the programmable target signals generated by the device of FIG. 3.

The automatic sensitivity control of the preferred embodiment is best illustrated with respect to FIGS. 3 and 4. An exemplary cardiac signal 130 whose peak amplitude is falling over time is shown in relation to an outer target reference voltage 132 supplied by programmable outer target 122 and an inner target reference 134 supplied by programmable inner target 126. The cardiac signal 130 shown is referred to as an electrogram and includes a number of cardiac cycles with each cycle including a peak voltage 136. In the exemplary electrogram of FIG. 4, the magnitude of the peaks 136 are generally diminishing from one cardiac cycle to the next. Processor 110 preferably tracks the fluctuations of the cardiac signal 130 by adjusting the outer target reference voltage 132 and inner target reference voltage 134 in concert with the cardiac signal 130. The processor 110 effectuates the changes in the inner and outer targets 132, 134 via control signals on lines 124, 128. Accordingly, the programmable targets 122, 126 are directed by processor 110 to generate the desired reference voltages 132, 134 generally following the decrease in the amplified cardiac signal 130. Adjustments to the target voltages 132, 134 may be made in discrete, step-wise increments as illustrated in FIG. 4, or may be smooth and continuous depending on the choice of circuit implementations for target logic units 122, 126.

Referring still to FIGS. 3 and 4, each time the cardiac signal 130 exceeds the inner target 134, inner comparator 108 produces a logic high signal on line 109 to processor 110. Likewise, outer comparator 106 generates a logic high signal on line 107 when the cardiac signal 130 exceeds the outer target reference voltage 132. By monitoring the output signals of comparators 106, 108 on lines 107, 109, the processor 110 can determine whether the peak 136 of each cardiac cycle is less than both inner and outer targets 134, 132, between the targets, or greater than the outer target 132. The processor 110 preferably adjusts the sensitivity of the sense circuit by adjusting the target reference voltages 132, 134 so that the peaks 136 are between the targets and preferably approximately equal to the outer target 132.

Accordingly, by this adjustment process, the outer target reference voltage 132 is approximately equal to the peaks 136 of the cardiac signal 130. Thus, the outer target reference 132 is a close approximation of the magnitude of the peaks 136 of the electrogram. As described above, the processor 110 controls the magnitude of the outer target 132. Preferably, processor 110 stores representations of the outer target reference magnitude in memory 120, or other programmable memory internal to the processor. The outer target representations stored by the processor 110 in memory 120 preferably are digital representations of the magnitude of the outer target reference signal at the peaks 136 of each cardiac cycle. Thus, the outer target representations may include a time series of outer target values obtained over a predetermined period of time. These values thus approximate the cardiac signal peaks 136 and indicate the change of the peaks over time. This information can be retrieved at a later time and transmitted to the external programmer 400 for viewing on display 408 (FIG. 2). A physician is thus provided with a close approximation of the electrogram. This information typically will be used by the physician to place limits on the pacer's automatic sensitivity control capability in accordance with known techniques. The limits are imposed by control signals transmitted by the programmer 400 to the pacer 100 via coils 111, 403. Where discrete, step-wise increments are used for target voltages, there will be a finite, brown number of settings, which can be represented by cells in memory. Incrementing the value stored in a cell whenever a particular setting occurs retains information about the waveform itself. In our preferred embodiment, the steps need not be equal in size or magnitude. Small steps are preferred where the magnitude of the signal is small; large steps, where the signal is large.

Figure 5:
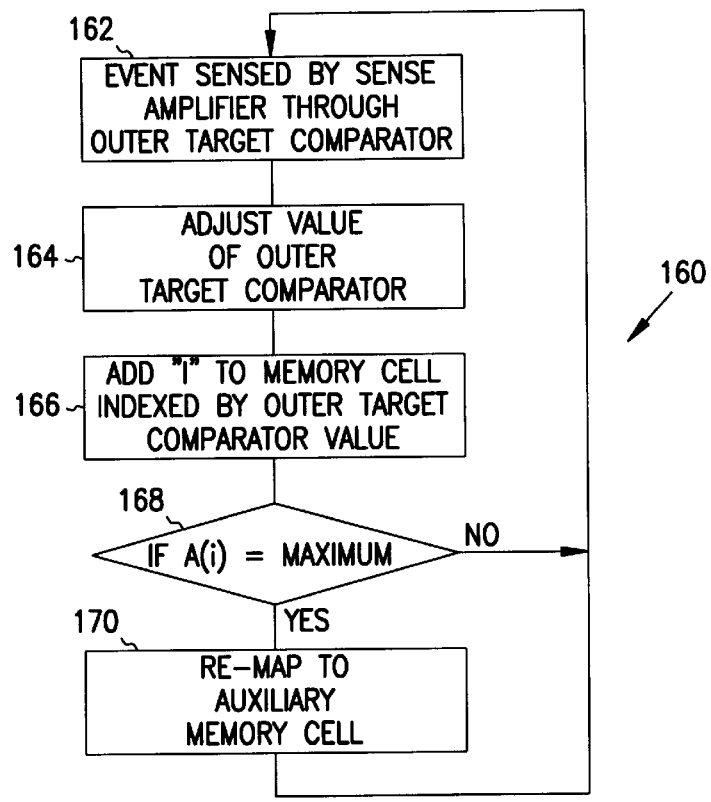
FIG. 5 is a flow chart of a program for storing target signal values.

The processor 110 stores on an on-going basis values for a histogram of the number of cardiac cycles pertaining to each outer target sensitivity level. A portion of the processor's operation is illustrated by the flow chart 160 of FIG. 5. A cardiac event is sensed 162 by the sense amplifier 102. In a known manner, the value of the outer target comparator is adjusted 164. Adjusting the outer target comparator is described, for example, in U.S. Pat. No. 5,103,819, incorporated herein by reference. A memory cell is associated with each value the outer target comparator can assume. Alternatively, if the value of the outer target comparator is varied continuously, a cell would be associated with a range of comparator values. During each cycle, the contents of the cell associated with the value of the comparator 166 during that cycle is incremented by one. It is anticipated that certain values will recur more frequently than others. In order to preserve memory, the processor checks 168 if the value in the incremented memory cell A(i) has exceeded its maximum. If so, a new memory cell will be assigned 170 and the number of occurances would continue to be counted. Thereafter, the processor would execute other programming, eventually returning to step 162 in the next cardiac cycle.

Figure 6:
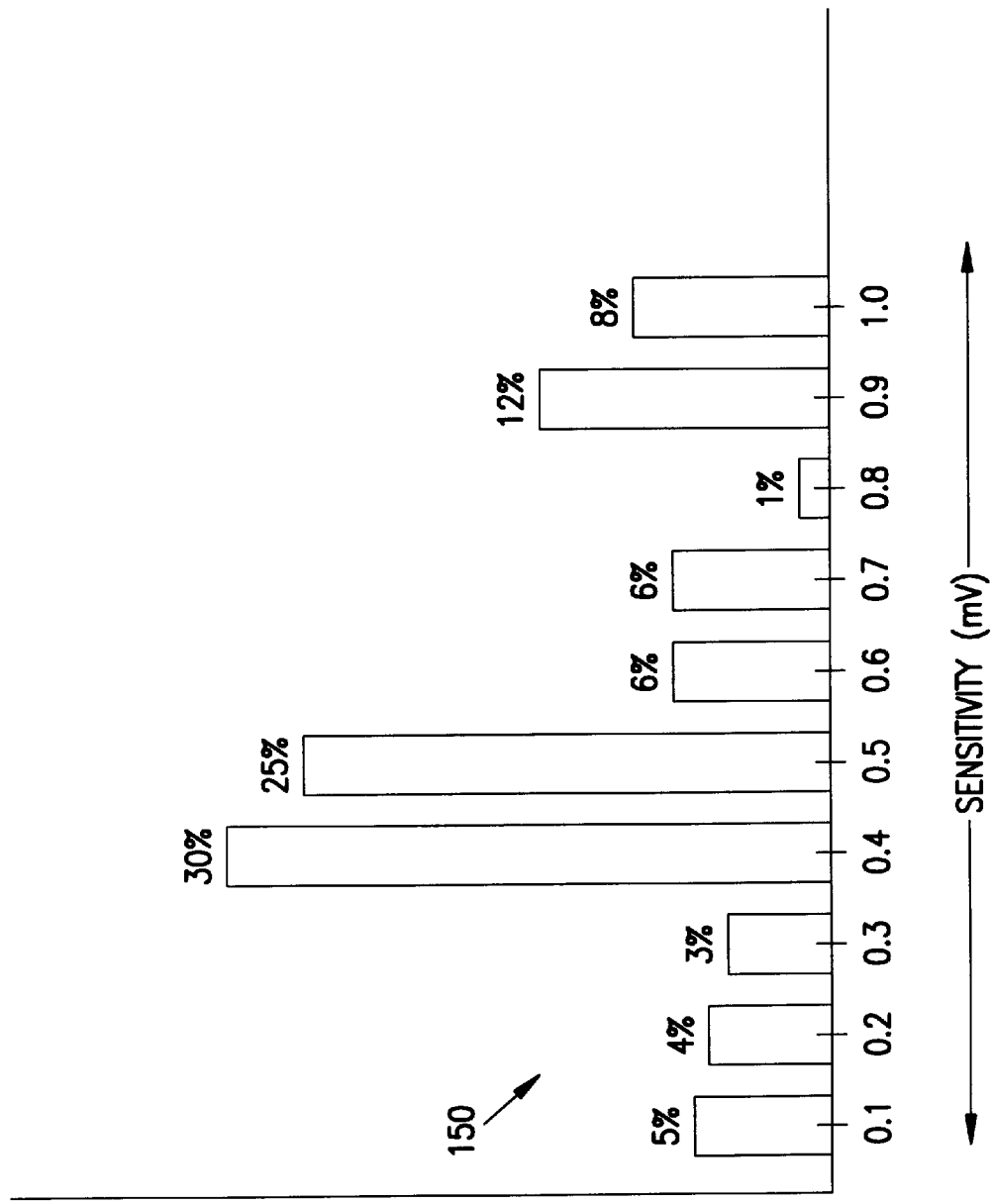

An exemplary histogram 150 is shown in FIG. 6. The relative number of cardiac cycles, expressed in percentages, is shown for ten different outer target sensitivity settings. As shown, 5% of the cardiac cycles occurring during a predetermined period of time occurred at an outer target setting of 0.1 mv, 3% occurred at an outer target of 0.2 mv, and so on. The period of time tracked by histogram 150 may be programmed by the physician or preset. Processor 110 computes the values for histogram 150 and stores that data in memory 120 for subsequent retrieval by a physician via external programmer 400. Histogram 150 is valuable to a physician and is particularly useful for appropriately setting the sensitivity level for the pacemaker to account for variations in IEGM amplitude throughout period, more representative of the normal variations than the short follow-up visit.

In the preferred embodiment, the programmer 400 receives data from the pacer 100 comprised of a series of numbers A(i) stored in memory cells indexed from $i_{min}$ to $i_{max}$, for the values of the comparator, as described above. Each number A(i) represents the number of times a particular value of the comparator occurred. The programmer computes the total number N of cycles, calculates percentages for each value of the comparator, and displays this information as a histogram.

Figure 7:
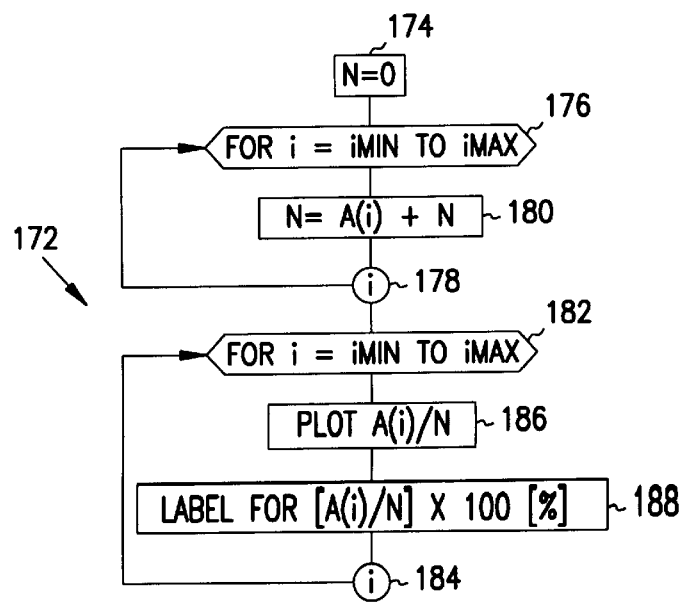
FIG. 6 is an exemplary histogram computed by the implantable medical device of FIG. 3 using a programmable sensing threshold as an estimate of the amplitude of the cardiac signal and FIG. 7 is a flow chart of a program for displaying a normalized histogram of stored target values.

This is illustrated in FIG. 7 in a program flow chart 172. The number N is cleared 174 to zero. The program loops 176 from $i_{min}$ to $i_{max}$, incrementing 178 i, thereby pointing at each number A(i). The numbers are added 180 together to obtain N, the total number of cardiac cycles. The program again loops 182 from $i_{min}$ to $i_{max}$, incrementing 184 i. The ratio of A(i)/n is computed 186 for each A(i) and plotted. The plot is labeled 188 in an appropriate manner.

Thus, the preferred embodiments described above advantageously provide a physician with needed information to monitor and adjust the sensitivity of an implanted pacer and create a histogram of sensitivities. Rather than measuring and storing the amplitudes of the cardiac signal itself, the pacer 100 stores the outer target reference values determined while the processor automatically adjusts the sensitivity of the sensing circuit. The sense circuit's outer target sensitivity setting is assumed to be a close approximation to the information the physician needs, and thus no additional circuitry is needed to obtain the desired information. Thus, the physician is provided with needed information from an implantable device that includes simpler circuitry and consumes less power than prior art devices.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device adapted to be implanted in the human body for electrically stimulating the heart to beat, comprising:

a plurality of electrodes;

a sense circuit coupled to at least one electrode of said plurality of electrodes for conditioning electrical signals from the electrode, said sense circuit including a comparator for comparing electrical signals from said electrodes to a programmable target signal;

a memory; and a processor having means for setting the magnitude of said target signal and means for storing representations of the frequency of occurrences of the set magnitudes of said target signal in said memory.

2. The medical device of claim 1 wherein said processor computes a histogram of the relative number of cardiac cycles associated with particular magnitudes of said target signal that occur over a predetermined period of time.

3. The medical device of claim 1 wherein in said processor computes a histogram of the absolute number of cardiac cycles at particular magnitudes of said target signal that occur over a predetermined period of time and stores said histogram in said memory.

4. A method for monitoring a patient's heart, comprising:

amplifying a cardiac signal;

comparing said amplified signal to an adjustable reference signal;

adjusting said reference signal to one of a plurality of magnitudes in response to said step of comparing said signal; and storing representations of the frequency of occurrences of each of said magnitudes of said reference signal in a memory device.

5. The method of claim 4 further including computing a histogram of the relative number of cardiac cycles associated with particular magnitudes of said target signal that occur over a predetermined period of time and storing said histogram in said memory device.

6. The method of claim 4 further including computing a histogram of the absolute number of cardiac cycles at particular magnitudes of said target signals that occur over a predetermined period of time.

7. The method of claim 5 further including retrieving said representations from said memory device and transmitting the representations to a programmer.

8. The method of claim 7 further including retrieving said histogram from said memory device and transmitting said histogram to said programmer.

9. An implantable medical device for electrically stimulating a human heart and monitoring said heart, including:

a plurality of electrodes;

a sense circuit coupled to said electrodes to condition electrical signals from said electrodes, said sense circuit including a comparator for comparing said electrical signals to one of a plurality of threshold targets;

a pulse generator adapted to generate pacing pulses;

a processor having means for setting said threshold target and means for computing a histogram of the relative number of cardiac cycles associated with particular settings of said threshold targets occurring over a predetermined period of time; and a memory device for storing said histogram.

* * * * *